(12) United States Patent
Allard et al.

(10) Patent No.: US 7,321,860 B2
(45) Date of Patent: Jan. 22, 2008

(54) SERVICE OFFERING FOR THE DELIVERY OF INFORMATION TO THE RIGHT RECEIVERS AT THE RIGHT TIME

(75) Inventors: David J. Allard, Boynton Beach, FL (US); Robert M. Szabo, Boca Raton, FL (US); James J. Toohey, Boca Raton, FL (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 11/025,823

(22) Filed: Dec. 27, 2004

(65) Prior Publication Data

US 2006/0143127 A1  Jun. 29, 2006

(51) Int. Cl.
G06Q 10/00 (2006.01)
G06Q 50/00 (2006.01)

(52) U.S. Cl. .................. 705/2; 705/3; 705/1
(58) Field of Classification Search ............ 705/2, 705/3, 51
See application file for complete search history.

(56) References Cited

U.S. PATENT DOCUMENTS

| | | | |
|---|---|---|---|
| 4,706,190 A | 11/1987 | Bomba et al. | |
| 5,517,405 A * | 5/1996 | McAndrew et al. | 706/45 |
| 6,359,888 B1 | 3/2002 | Koch et al. | |
| 6,421,650 B1 * | 7/2002 | Goetz et al. | 705/3 |
| 6,463,417 B1 * | 10/2002 | Schoenberg | 705/2 |
| 6,482,156 B2 * | 11/2002 | Iliff | 600/300 |
| 6,757,898 B1 * | 6/2004 | Ilsen et al. | 718/203 |
| 2002/0147646 A1 * | 10/2002 | Ogura et al. | 705/14 |
| 2003/0041031 A1 * | 2/2003 | Hedy | 705/51 |
| 2003/0130867 A1 * | 7/2003 | Coelho et al. | 705/2 |
| 2003/0208391 A1 * | 11/2003 | Dvorak et al. | 705/8 |
| 2003/0220817 A1 * | 11/2003 | Larsen et al. | 705/2 |
| 2004/0068421 A1 * | 4/2004 | Drapeau et al. | 705/2 |
| 2004/0210458 A1 * | 10/2004 | Evans et al. | 705/2 |

OTHER PUBLICATIONS

Kim, J., et al., "Integrated Multimedia Medical Data Agent in E-Health", Australian Computer Society, 2002.
Lieberman, H., "Intelligent Agent Software for Medicine", IOS Press, Amsterdam, 2002.
Nealon, J.L., et al., "The Application of Agent Technology to Health Care", Bologna, Jul. 2002.

* cited by examiner

Primary Examiner—Andrew J. Fischer
Assistant Examiner—Nancy T. Le
(74) Attorney, Agent, or Firm—Akerman Senterfitt

(57) ABSTRACT

A method for providing information to requestors that includes the step of receiving a request from a remotely located information requestor. The request can be associated with an information controller and with a designated purpose. A transaction can be initiated to handle the request and to deliver a result to an information receiver. A record store can be queried for information associated with the information controller and associated with the designated purpose. The information requestor and the information receiver may not be authorized to directly access content of the record store. At least one request result can be generated based at least in part upon information returned from the querying step. Each request result can correspond to each information receiver and be tailored for information privileges of the information receiver. The information privileges can be established by the information controller. The request result can be conveyed to the information receiver.

19 Claims, 6 Drawing Sheets

| 210 | Transaction ID |
|---|---|
| | Transaction Owner |

| 220 | Transaction Type A |
|---|---|
| | Transaction Receiver A |
| | Results Receiver A1, A2, ... Ax |
| | Results Delivery Schedule A1, A2, ... Ax |
| | Results Expiration Time Stamp A1, A2, ... Ax |

| 230 | Transaction Type B |
|---|---|
| | Transaction Receiver B |
| | Results Receiver B1, B2, ... By |
| | Results Delivery Schedule B1, B2, ... By |
| | Results Expiration Time Stamp B1, B2, ... By |

•
•
•

| 240 | Transaction Type N |
|---|---|
| | Transaction Receiver N |
| | Results Receiver N1, N2, ... Nz |
| | Results Delivery Schedule N1, N2, ... Nz |
| | Results Expiration Time Stamp N1, N2, ... Nz |

FIG. 2

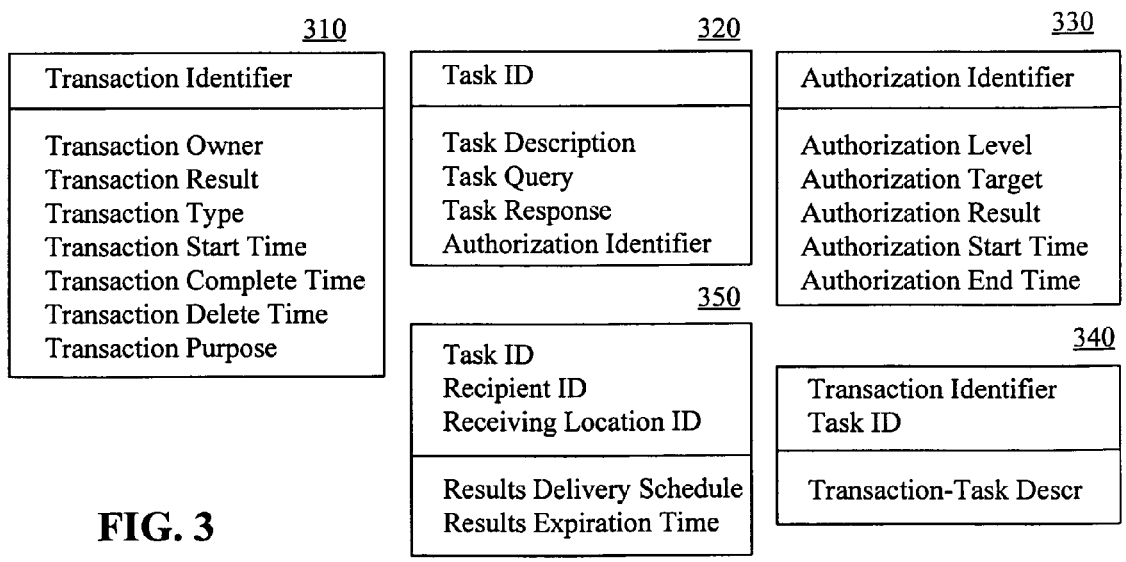

FIG. 3

SERVICE OFFERING FOR THE DELIVERY OF INFORMATION TO THE RIGHT RECEIVERS AT THE RIGHT TIME

BACKGROUND

1. Field of the Invention

The present invention relates to the field of information management and, more particularly, to a controlled methodology for providing information to the right receivers at the right time.

2. Description of the Related Art

The information age is all about information exchanges, with an ultimate goal of providing information receivers with desired information upon demand in a reasonable fashion. Conflicting concerns, however, make this goal difficult to achieve. For example, information controllers often do not wish to give out information of value to information receivers, where valuable information can include private or confidential information about an individual as well as intellectual property owned or controlled by a business entity. Other conflicting concerns include concerns of information accessibility versus security, information breadth versus accuracy, and information completeness versus timely delivery of information.

Conventional data exchanges have focused upon granting individuals access to data contained within designated data repositories. Access is usually granted in a broad stroke, such as granting read, write, and update privileges to users against the entire or designated portions of each data repository. Further, a data storage methodology is generally selected that optimizes the data within the data repository for a single platform and storage methodology. Conventional exchanges focus upon synchronizing disparate data stores to share data contained within the stores. Simply put, conventional exchanges are data-centric exchanges that focus upon manipulating bits and bytes as opposed to information-centric concerns.

Consequently, information is currently being stored in a manner and fashion tailored for computers and not necessarily tailored for the needs of information receivers and information controllers. These entities care more about having the right information available to the right receivers, and only the right receivers, at the right time, and only at the right time. Conventional data processing and manipulation systems are inadequately designed to accomplish these information processing goals.

SUMMARY OF THE INVENTION

The present invention discloses a method, system, and apparatus for processing information, ensuring that the right information is delivered to the right receivers at the right time, where each information receiver can represent an information recipient (such as a person or entity), an information location (such as a location specified by a network address), and combinations thereof. More specifically, an information service can communicatively link a plurality of remotely located entities connected to an information service through network connections. The information service can maintain a local record store of information and can interact with remotely located information providers. Information requestors contacting the local record store can submit an information request. The request can specify a designated purpose for the request, one or more recipients for the request, and a time that a result for the request is needed.

The information service can then generate one or more request results, each to be delivered to a particular information recipient, where the results can be tailored for the information privileges granted to the information recipient by one or more information controllers. Information conveyed by the information service can be accessible for a limited time in accordance with the designated purpose of the request. When the limited time expires or when the designated purpose has been satisfied, information conveyed by the information service can be automatically deleted from any data store accessible by the information recipient.

One aspect of the present invention can include a method for providing information to requestors that includes the step of receiving a request from a remotely located information requestor. The request can be associated with an information controller and with a designated purpose. A transaction can be initiated to handle the request. The transaction can identify at least one remotely located information recipient to receive a request result. A record store can be queried for information associated with the information controller and associated with the designated purpose. The information requestor and the information recipient can be parties not authorized to directly access content of the record store. At least one request result can be generated based at least in part upon information returned from the querying step. Each request result can correspond to each information recipient and can be tailored for information privileges of the information recipient. The information privileges can be established by the information controller. The request result can be conveyed to the information recipient.

Another aspect of the present invention can include an information service system for providing results responsive to requests. Each request can be associated with an information controller and a designated purpose. The results can be tailored to authorization privileges granted by the information controller to the information recipient. The information service system can include an information repository that includes information that is not directly accessible by a remote system from which requests originate and that is not directly accessible by a remote system to which results are conveyed. Instead, the information service system provides only that information necessary for satisfying an information request, and provides that information for only the duration necessary to achieve the designated purpose.

Still another aspect of the present invention can include an information client that includes an information presentation application. The information presentation application can present results supplied by a remotely located information service system. The results can be generated by the information service system responsive to information requests from a source other than the information client. The results for the requests can be specifically tailored to privileges an information controller granted to an information recipient. The information recipient can be the information presentation application user. The results presented within the information presentation application can be automatically deleted upon an occurrence of an event. The information presentation application can be configured so as to be unable to retain a local copy of the results after the occurrence.

It should be noted that the invention can be implemented as a program for controlling a computer to implement the functions described herein, or a program for enabling a computer to perform the process corresponding to the steps disclosed herein. This program may be provided by storing the program in a magnetic disk, an optical disk, a semiconductor memory, any other recording medium, or distributed via a network.

BRIEF DESCRIPTION OF THE DRAWINGS

There are shown in the drawings, embodiments which are presently preferred, it being understood, however, that the invention is not limited to the precise arrangements and instrumentalities shown.

FIG. 2 details illustrative data constructs in accordance with an embodiment of the present invention.

FIG. 3 details illustrative data structures for transaction, task, authorization, transaction-task linkage, and transaction-receiver linkage in accordance with an embodiment of the present invention.

DETAILED DESCRIPTION OF THE INVENTION

Figure 1:
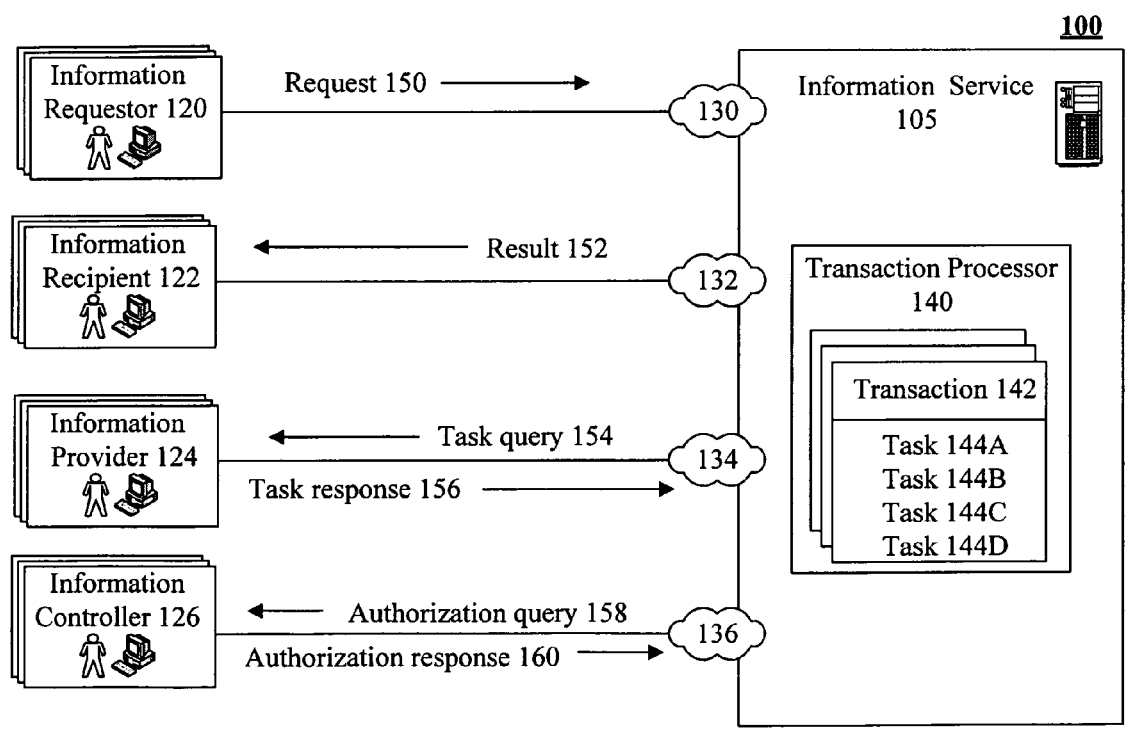
FIG. 1 is a schematic diagram for a system that delivers information in a controlled fashion in accordance to an embodiment of the inventive arrangements disclosed herein.

FIG. 1 is a schematic diagram for a system 100 that delivers information in a controlled fashion in accordance to an embodiment of the inventive arrangements disclosed herein. In system 100, one or more information requestors 120 can submit a request 150 over network 130 to information service 105. Each request 150 can specify a need for information controlled by one or more information controllers 126. Request 150 can also have a designated purpose and one or more target information recipients 122.

Information service 105 can use transaction processor 140 to initiate a transaction 142 to handle request 150. That is, transaction 142 can generate one or more results 152 for request 150 that is specifically tailored for the designated purpose. Result 152 can also include information associated with information controller 126. Result 152 can be conveyed over network 132 to one or more information recipients 122. Each result 152 can be tailored for the information privileges of the target information recipient 152 and can include only that information related to the designated purpose.

Transaction 142 can utilize one or more tasks in generating the result 152. For example, transaction 142, can utilize task 144A, task 144B, task 144C, and task 144D. The transaction processor 140 can process tasks 144A, 144B, 144C, and 144D in series and/or in parallel, depending upon transaction 142 specifications.

One or more of tasks 144A, 144B, 144C, and 144D can query a record store internal to the information service 105. Additionally, one or more of tasks 144A, 144B, 144C, and 144D can convey task query 154 over network 134 to information provider 124 that responsively provides task response 156. Task query 154 can initiate an information retrieval operation, an information confirmation operation, an information search operation, or any other information function that information provider 124 is configured to provide. The resulting information can be included in task response 156, which can be used to generate result 152.

Further, task query 154 can trigger the information provider 124 to perform a programmatic action related to the designated purpose. This programmatic action need not be specifically tailored to provide information used in the construction of the result 152, but can instead adjust an environmental state that furthers the designated purpose. Accordingly, the task response 156 can indicate a result of the programmatic action that furthers the designated purpose or can indicate an environmental state related to the designated purpose.

Since each result 152 and even each task query 154 can include information controlled by an associated information controller 126, a means to ensure that no entity receives unauthorized information is necessary. To this end, the information service 105 can convey an authorization query 158 across network 136 to information controller 126. The information controller 126 can responsively convey authorization response 160 to the information service 105 via network 136.

Only information which is authorized (as determined by an authorization response 160) for an information target (which can include an information recipient 122 and an information provider 124) is conveyed by the information service 105 to a designated information target. The authorization response 160 can authorize an information target to receive information for a one-time event or can grant continuous access. Further, the authorization response 160 can authorize a single information target or can authorize a category of information targets. Moreover, the authorization signified by the authorization response 160 can include temporal or purpose-specific constraints, which authorize access to an information target only when conditions related to the constraints are satisfied.

In one embodiment, to ensure the result 154 is conveyed to a proper information receiver (comprising a target information recipient 122, a target location, and combinations thereof), the information service 105 can determine a suitable delivery location for the result 152. For example, when the result 152 is to be presented to an information recipient 122 immediately before a meeting, a suitable delivery location could include the meeting location, which means that the results 152 could be conveyed to a computing device that the information recipient 122 can access from the meeting location. When the same result 152 is to be presented to the information recipient 122 a few days before the meeting, a suitable delivery location could include a work location of the information recipient 122. Consequently, information service 105 can selectively provide results 152 to different information delivery locations depending on a time of delivery for the results 152.

Each of the information requestor 120, the information recipient 122, the information provider 124, and the information controller 126 can include a person, a business entity, or an organization as well as a computing system, a computing device, an information service, or an information repository.

Networks 130, 132, 134, and 136 can represent any communication mechanism capable of conveying digitally encoded information. Each of the networks 130, 132, 134, and 136 can include a telephony network like a Public Switched Telephone Network (PSTN) or a mobile telephone network, a computer network like a local area network or a wide area network, a cable network, a satellite network, a broadcast network, and the like. Further, each of the networks 130, 132, 134, and 136 can use wireless as well as line-based communication pathways. Digitally encoded information can be conveyed via network 130, 132, 134, or 136 in accordance with any communication protocol, such as a packet-based communication protocol or a circuit based communication protocol.

Additionally, information conveyance across networks 130, 132, 134, and 136 can occur in an open or secured fashion. For example, communications over networks 130, 132, 134, and 136 can use Secured Socket Layer (SSL) connections, can use private/public key encryption techniques, and can utilize Virtual Private Network (VPN) technologies.

FIG. 2 details illustrative data constructs in accordance with an embodiment of the present invention. While the data structures of FIG. 2 can be used by the information service 105 of FIG. 1, the invention is not to be limited in this regard.

More specifically, the data constructs of FIG. 2 define a new transaction type for coordinating information conveyances to assure information is provided to the right information receivers at the right time. The new transaction type identifies the owner of the transaction and can identify multiple parties that are to perform work for the transaction. Each of the multiple parties (transaction receiver) can receive a transaction specification tailored for that party. That is, for each transaction identifier an associated transaction type, a transaction receiver, one or more results receivers, one or more results delivery schedule entries, and one or more results expiration time stamps can be specified. Accordingly, the data construct of FIG. 2 identifies the owner of a transaction, the parties who are to do work, what type of work they are to do, where they are to send their results, when they are to send their results, and how long the results are good for.

In operation, it is envisioned that a person can initiate a request through his or her computer, PDA, phone, or other such device. The device (or a server to which the device was connected) can build a transaction request as depicted in FIG. 2. The transaction request can be conveyed to other parties (that can include one or more computers) involved in the transaction telling the parties what to do (e.g., search, compute, verify, etc.), when results are needed, and where to send the results. Additionally, the transaction request can specify the life span of the results. It should be noted that results may be sent to multiple parties, each result having a unique life span. Consequently, each recipient can know the duration for which results should be kept available to receivers and when the results should be disposed of, thereby freeing up local resources.

FIG. 3 details illustrative data structures for transaction 310, task 320, authorization 330, transaction-task linkage 340, and transaction-receiver linkage 350 in accordance with an embodiment of the present invention. The data structures of FIG. 3 can represent one embodiment for the data constructs presented in FIG. 2. It should be appreciated, however, the data constructs of FIG. 2 can be implemented in any of a variety of data structures and are not to be construed as limited to the embodiment presented in FIG. 3, which is provided for illustrative purposes.

Transaction 310 can store data fields pertaining to individual transactions associated with one or more issued requests. Each transaction 310 can include a unique transaction identification key. Further, transaction 310 can include any of a variety of data attributes like a transaction owner, a transaction result, a transaction type, a transaction start time, a transaction complete time, a transaction delete time, and a transaction purpose.

The transaction owner can be the information requestor that submitted a request which initiated the transaction. The transaction result can be the result generated in answer to the request. The transaction type can be one of a variety of previously established transaction types handled by the information service 105. Different tasks 320 and different information receivers can be associated with each transaction type. The transaction purpose can indicate a purpose for which a corresponding transaction was initiated, which can be different from the transaction type. In one embodiment, transaction results can be deleted from a data store accessible by the information recipient once the transaction purpose has been satisfied.

The transaction start time can represent a time at which the transaction begins and can be used for scheduling purposes. The transaction complete time can specify a time a transaction is to finish processing a request. The transaction delete time can indicate a time at which the transaction results are to be deleted from an information recipient's information store.

Task 320 can include information for each task spawned to produce a task response that is used when generating a transaction result. Task 320 can have a unique task identifier and attributes like a task description, a task query, a task response, and an authorization identifier. The authorization identifier can be a foreign key linking a task to authorization 330.

Linkage 340 can associate a transaction 310 with a task 320 in a one-to-one, one-to-many, many-to-one, and many-to-many fashion. Each association of linkage 340 can include a transaction-task description.

Linkage 350 can associate a task 320 with one or more information receivers. An information receiver can be specified by a recipient identifier and a receiving location identifier. Each association of linkage 350 can include a results delivery schedule and a results expiration time.

Authorization 330 can include information necessary to permit an associated transaction 310 or task 320 to execute. Further, the authorization 330 can signify information privileges for an information receiver. Authorization 330 can include an authorization identifier, an authorization level, an authorization target, and an authorization result. Since the authorization 330 can be established for a designated period or purpose, the authorization 330 can have one or more fields constraining an authorization, such as an authorization start time and an authorization end time.

Figure 4:
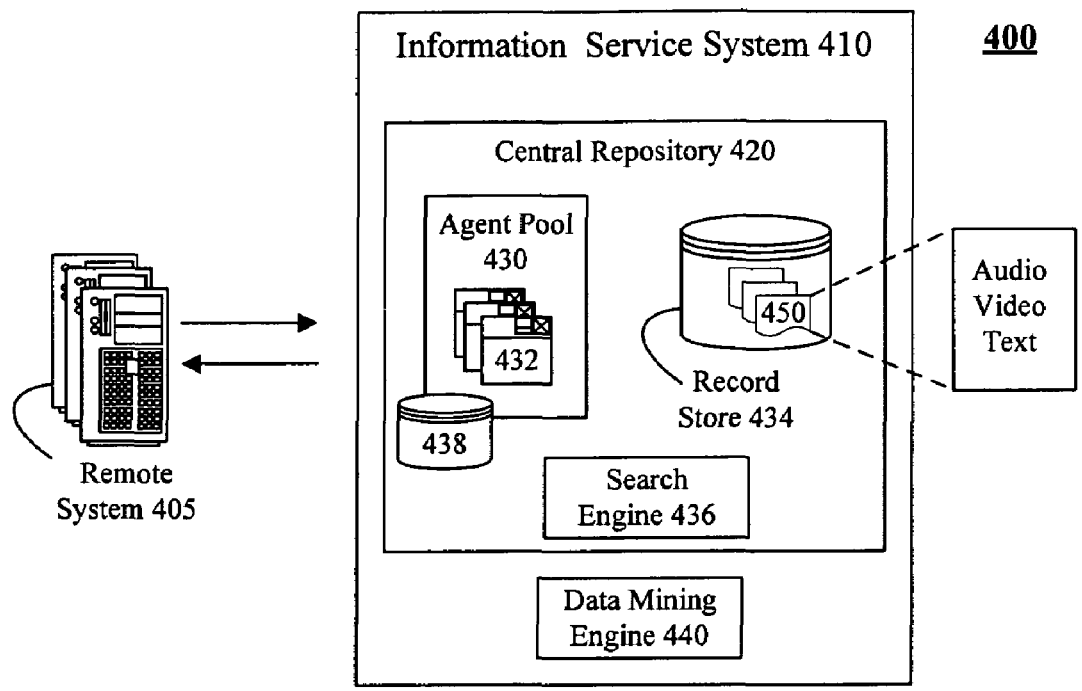
FIG. 4 is a schematic diagram of an information service system that interacts with one or more remote systems in accordance with an embodiment of the inventive arrangements disclosed herein.

FIG. 4 is a schematic diagram of a system 400 of an information service system 410 that interacts with one or more remote systems 405 in accordance with an embodiment of the inventive arrangements disclosed herein. Information service system 410 can provide information service 105 of FIG. 1. Moreover, remote systems 405 can represent the information requestor 120, the information recipient 122, the information provider 124, and the information controller 126 of FIG. 1. The invention, however, is not to be limited in this regard.

The information service system 410 can include a central repository 420 in which information is stored. The information of the central repository 420 can be controlled so that information receivers only receive that information for which authorization has been granted by an information controller. Further, the information of the central repository 420 can be dispersed for a limited time in accordance with a designated purpose of the information as stated in an information request.

The information repository can include an agent pool 430 that provides a multitude of intelligent agents 432. Each intelligent agent 432 can manage one transaction at a time, where each transaction can produce a request result for a particular request. In producing a request result, the intelligent agent 432 can generate one or more tasks, such as an information retrieval task, an authorization task, an information validation task, and the like. The intelligent agents 432 can utilize data store 438 to store details concerning steps taken to generate a request result. For example, algorithms, information providers, search criteria, user preferences, authorization entries, and other such details can be recorded within the data store 438 by intelligent agents 432.

Further, intelligent agents 432 can retrieve information from record store 434 local to the central repository 420 and from remotely located information providers using tools like search engine 436. The record store 434 can maintain several records 450, each record can include audio, video, and graphics as well as textual information.

The search engine 436 can gather information from external information service systems, from the Internet or other online resource, from private networks, and other such sources. In one embodiment, information receivers can grant the information service 105 access to otherwise private information in return for using the service. In such an embodiment, the information receiver would be considered an information controller of this otherwise private information.

The data mining engine 440 can sort through data, such as data within the record store 434, data store 438, and remote data stores (not shown), to identify patterns and relationships contained within the data. Accordingly, the data mining engine 440 can "mine" a quantity of data to generate information from that data.

Notably, since the data mining engine 440 does not disseminate the data that it analyzes to information receivers, it is not necessary for the information controller to grant privileges against the raw data being analyzed by the data mining engine 440 in order for the data mining engine 440 to operate. Privileges must be granted, however, before information generated by the data mining engine 440 is conveyed to one or more information receivers. Consequently, the information generated by the data mining engine 440 can be a sanitized version of raw data from which the information was generated, where the sanitized version of information that is void of any details that an information controller has not authorized an information receiver to access.

Figure 5:
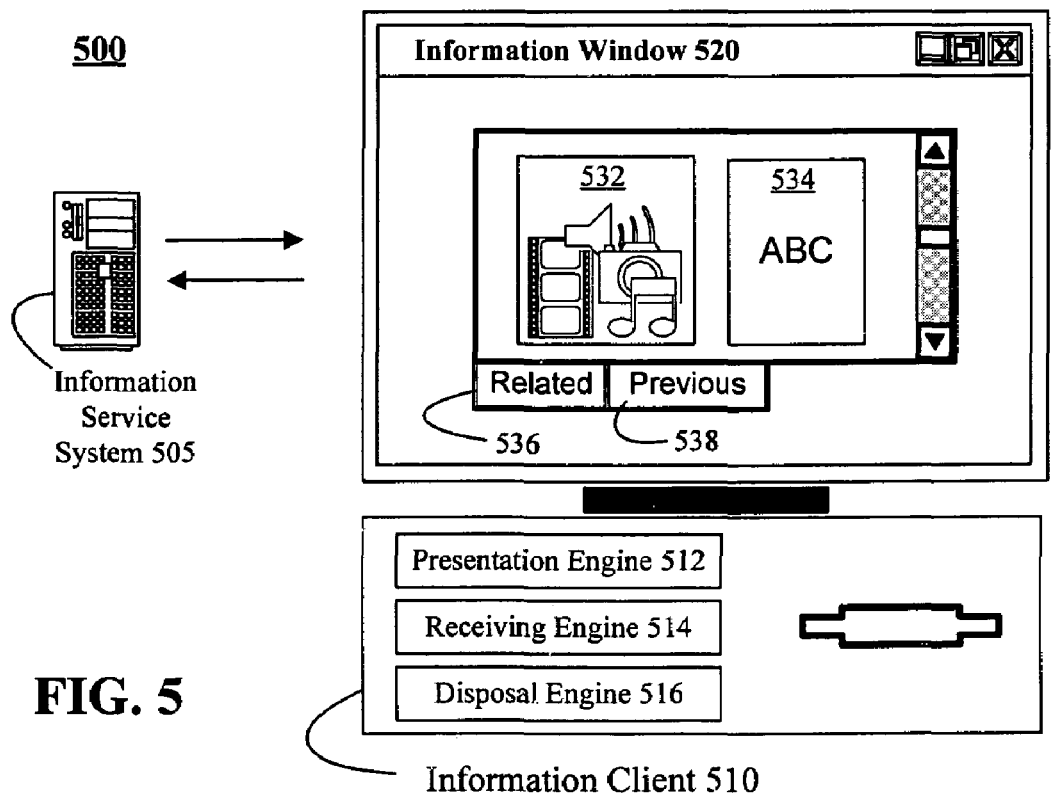
FIG. 5 is a schematic diagram of a client information system that interacts with an information service system in accordance with an embodiment of the inventive arrangements disclosed herein.

FIG. 5 is a schematic diagram of a system 500 of an information client 510 that interacts with an information service system 505. Information service system 505 can be the information service system 410 of FIG. 4. Additionally, the information client 510 can be a system through which one or more entities interact with the information service system 505. As such, the information client 510 can correspond to a system used by the information requestor 120, the information recipient 122, the information provider 124, or the information controller 126 of FIG. 1. The subject matter expressed and claimed herein, however, is not to be construed as being limited to the arrangements detailed within FIG. 5, which represents one of a variety of embodiments of the present invention.

The information client 510 can include an information window 520 in which information provided by the information service system 505 can be presented. The information window 520 can include digital media 532, like audio, video, and graphics, as well as text 534. Further, a user of the information window 520 can be provided an option to request related information 536, or to view previous 538 information provided by the information service system 505 in the past.

The information window 520 can also include a plurality of user specific settings (not shown) that permit customized information presentation. The user settings can also be used by the information service system 505 to generate information in a manner preferred by the user of the information window 520. Thus, the configuration settings can affect not only how information is presented, but can affect the content of the information provided to an information receiver as well.

The information client 510 can also include a presentation engine 512, a receiving engine 514, and a disposal engine 516. The presentation engine 512 can provide functions and routines used by the information window 520 to present information provided by the information service system 505. In one embodiment, the presentation engine 512 can provide security measures to ensure that information is only presented to authorized information receivers. For example, the information service system 505 can encrypt information conveyed to the information client 510, where the presentation engine 512 decrypts the information before presentation.

The receiving engine 514 can process incoming information for use by the information window 520. The receiving engine 514 can cache streamed content, can provide recovery mechanisms to re-initialize faulty transmissions, and can otherwise manage downloaded content.

The disposal engine 516 can ensure that information is erased from the information client 510 once the purpose for which the information was conveyed is satisfied. For example, information conveyed to the information client 510 can have an associated information expiration time or delete time that can activate the disposal engine 516. In another example, information can have a previously determined delete event associated with it. The delete event can be triggered either by processes within the information client 510 or by remotely located processes, such as an information service system 505 process.

Figure 6:
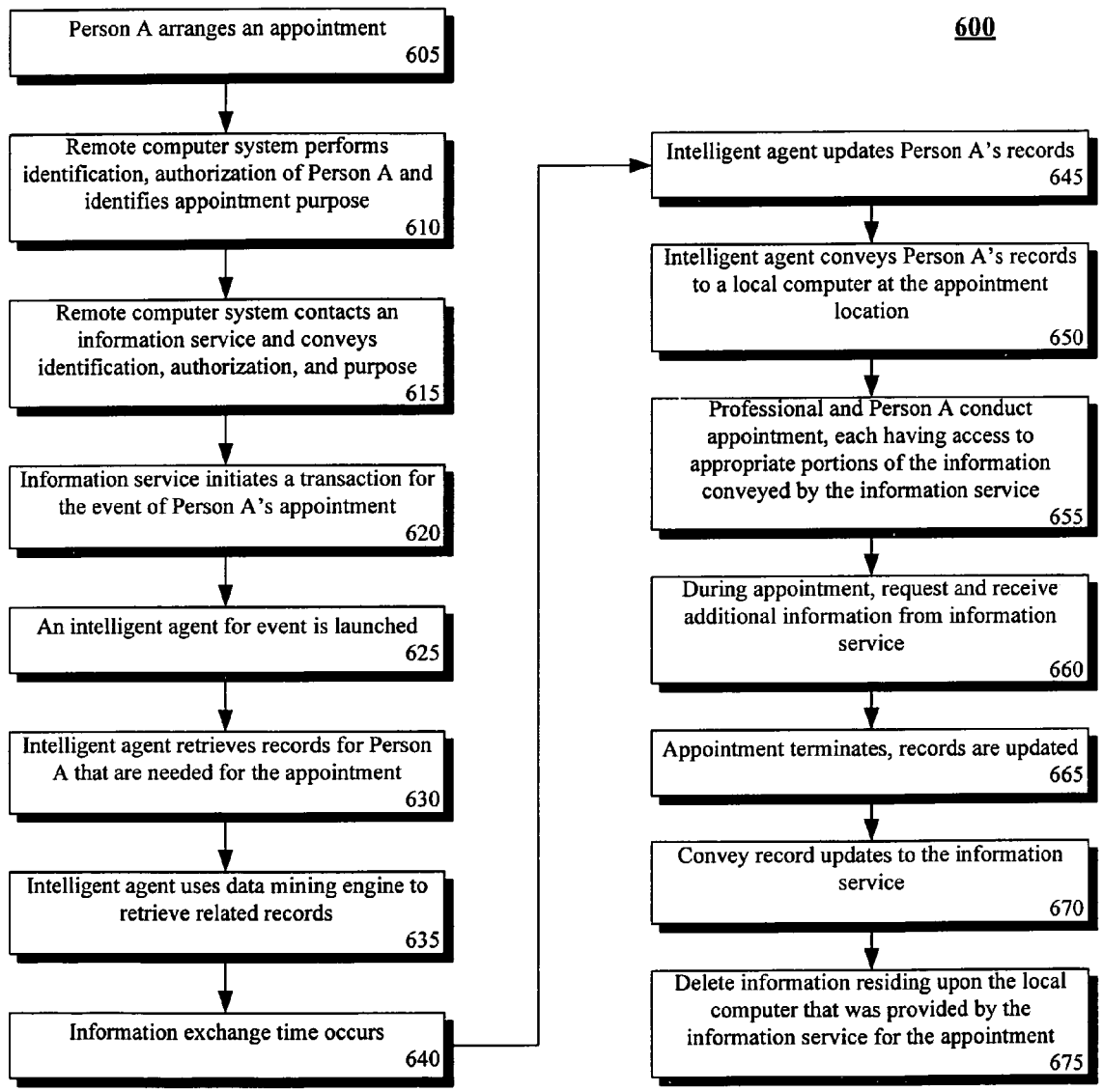
FIG. 6 is a flow chart illustrating an intelligent agent being utilized in accordance with an embodiment of the inventive arrangements disclosed herein.

FIG. 6 is a flow chart illustrating an interaction 600 showing the use of an intelligent agent in accordance with an embodiment of the inventive arrangements disclosed herein. The interaction 600 can be performed in the context of an information processing system, such as the system 100 or system 400.

Interaction 600 can begin in step 605, where a Person A can arrange an appointment. In step 610, a remote computer system can confirm the identity of Person A and can determine information for which Person A is authorized. The remote computer system can also identify the purpose of the appointment. In step 615, the remote computer system can contact an information service and can convey the identification, authorization, and purpose to the information service.

In step 620, the information service can initiate a transaction for an event, the event being Person A's appointment. In step 625, an intelligent agent for the event can be launched. In step 630, the intelligent agent can retrieve records for Person A that are needed for the appointment. In step 635, the intelligent agent can use a data mining engine to retrieve related records.

In step 640, the time to exchange information can occur. This can represent a time proximate to the appointment. In step 645, the intelligent agent can update Person A's records. In step 650, the intelligent agent can convey Person A's records to a local computer at the appointment location. In step 655, a professional with whom Person A is meeting and Person A can conduct the appointment. Both the professional and Person A can have access to appropriate portions of the information conveyed by the information service.

In step 660, during the appointment, a request for additional information can be generated. This request can be conveyed to the information service and more specifically to the intelligent agent, which can responsively provide additional information. In step 665, the appointment can terminate and local records can be updated. In step 670, these record updates can be conveyed to the information service and received by the intelligent agent. The intelligent agent can responsively update appropriate records within a data store of the information service. In step 675, information residing upon the professional's local computer can be deleted.

Figure 7:
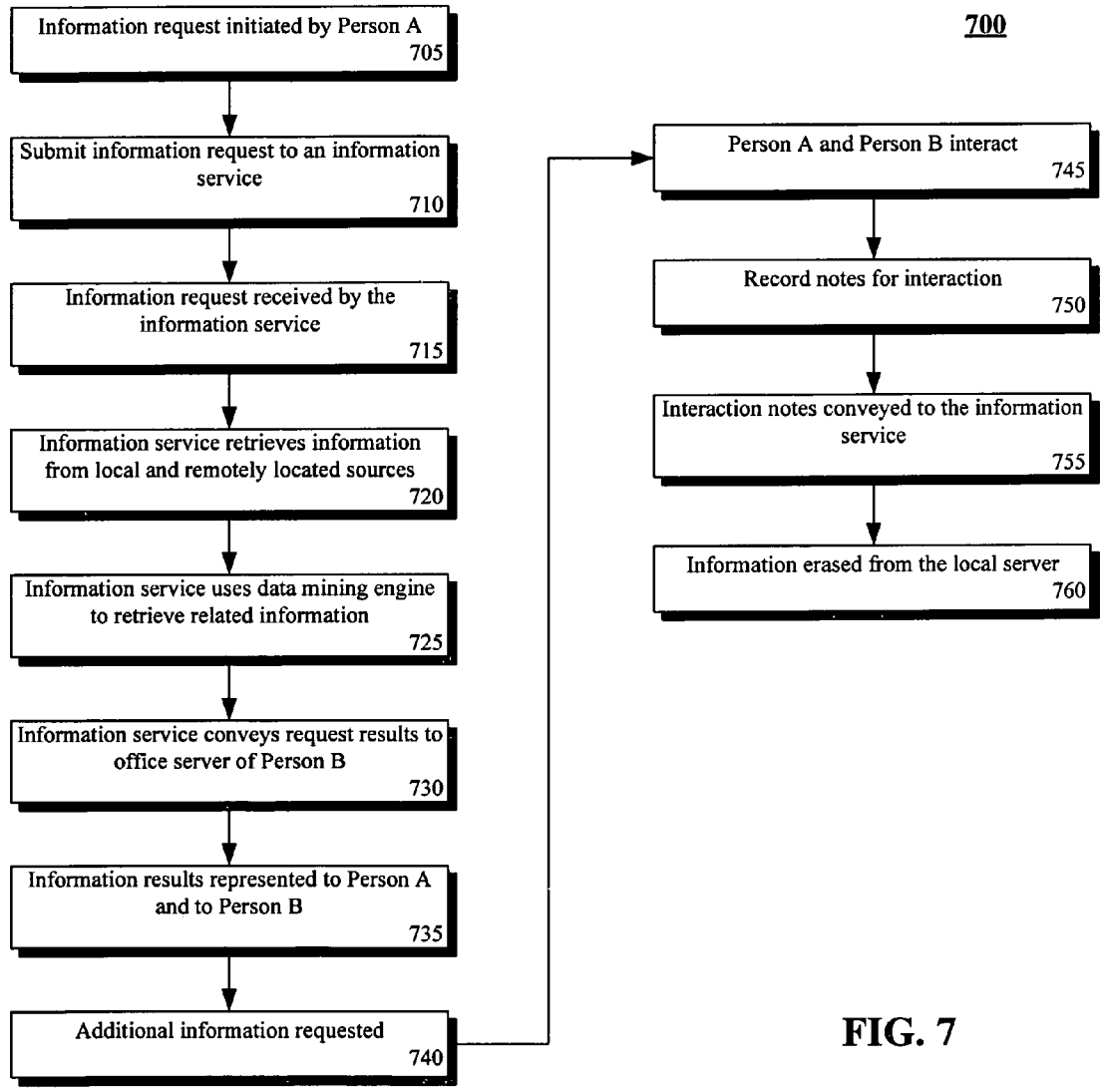
FIG. 7 is a flow chart illustrating an interaction between an information requestor and an information service in accordance with an embodiment of the inventive arrangements disclosed herein.

FIG. 7 is a flow chart illustrating an interaction 700 between an information requestor and an information service in accordance with an embodiment of the inventive arrangements disclosed herein. The interaction 700 can be performed in the context of an information processing system, such as the system 100 or system 400.

Interaction 700 can begin in step 705 where an information request is initiated by Person A. The information request can specify the purpose for the request and one or more information receivers. In step 710, the information request can be submitted to an information service. The request can be submitted by Person A, or by an entity that Person A interacts with. For example, if the purpose of the information request is for a doctor's appointment, either the patient (Person A) or the physician (Person B) can submit the information request to the information service.

In step 715, the information request can be received by the information service. In step 720, the information service can retrieve information from a local record store and from remotely located sources. In step 725, the information service can use a data mining agent to retrieve related information. In step 730, the information service can convey information for the doctor's appointment to a local office server of the doctor (Person B). In one embodiment, this information conveyance can be timed to coincide with the scheduled time of the patient's appointment with the doctor.

In step 735, information can be presented to both Person A (the patient) and Person B (the doctor) separately. Different information can be presented to each. For example, Person A (the patient) can be presented with address information, insurance information, and a medical history and prompted to confirm that the information is correct. This information can be presented while Person A is in the waiting room. Person B (the doctor) can be presented with patient records, test results, and an expert system's analysis of likely medical conditions relating to Person A. The patient records can include digital images (like X-rays), audio files, video, as well as text.

In step 740, either Person A or Person B from their respective interfaces can request additional related information or can confirm the accuracy of the presented information. Additionally, Person A and/or Person B can provide additional information. In step 745, Person A and Person B can interact. In step 750, both Person A and Person B can record interaction notes and results. In step 755, these notes can be conveyed back to the information service. In step 760, the information provided to Person A and Person B can be erased from local data stores (like the doctor's server).

Figure 8:
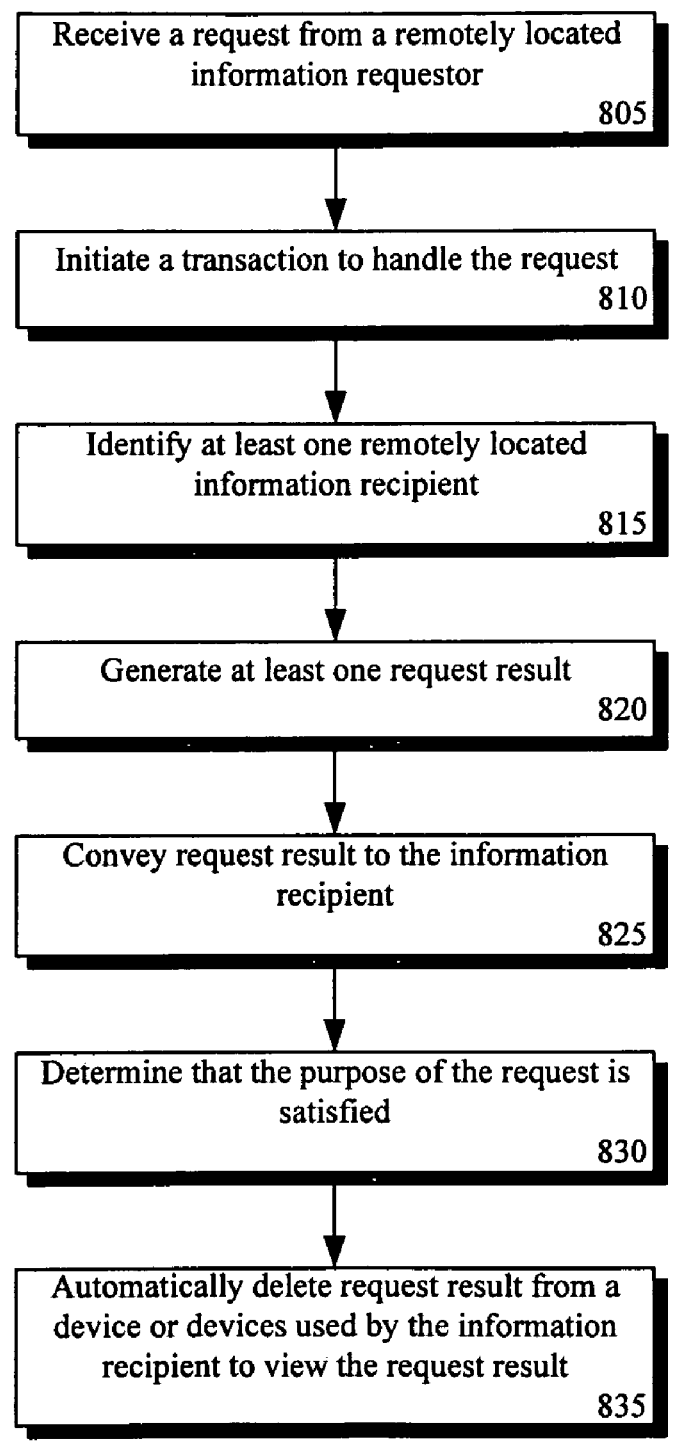
FIG. 8 is a flow chart illustrating a method for providing information to requestors in accordance with an embodiment of the inventive arrangements disclosed herein.

FIG. 8 is a flow chart illustrating a method 800 for providing information to requestors in accordance with an embodiment of the inventive arrangements disclosed herein. The method 800 can be performed in the context of an information processing system, such as the system 100 or system 400.

Method 800 can begin in step 805, where a request can be received from a remotely located information requestor. The request can be associated with an information controller and a designated purpose. The designated purpose can, for example, be a business transaction between the information controller and the information requestor. The information controller, the information requestor, and one or more information recipients can, however, be separate entities.

In step 810, an information service system, upon receiving the information request, can initiate a transaction to handle the request. In step 815, the transaction can identify at least one remotely located information recipient to receive the request result.

In step 820, at least one request result can be generated based upon information returned responsive to the record store queries. The request results can be tailored for the information privileges of the information recipient. These information privileges can be established by the information controller.

In step 825, the request results can be conveyed to the information recipient. In step 830, a determination can be made that the designated purpose for which the request results were generated has been satisfied. In step 835, responsive to this determination, the request results can be automatically deleted from the device or devices used by the information recipient to view the request results. After deletion, the request result can be erased from any data store that is directly accessible by the information recipient. In situations where it is not possible to erase conveyed records, an access key (previously used to access the request results) can be invalidated so that the information recipient can no longer view the results in an understandable fashion.

The present invention may be realized in hardware, software, or a combination of hardware and software. The present invention may be realized in a centralized fashion in one computer system or in a distributed fashion where different elements are spread across several interconnected computer systems. Any kind of computer system or other apparatus adapted for carrying out the methods described herein is suited. A typical combination of hardware and software may be a general purpose computer system with a computer program that, when being loaded and executed, controls the computer system such that it carries out the methods described herein.

The present invention also may be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

This invention may be embodied in other forms without departing from the spirit or essential attributes thereof. Accordingly, reference should be made to the following claims, rather than to the foregoing specification, as indicating the scope of the invention.

What is claimed is:

1. A method for an information service to provide information to requestors at a later designated time comprising the steps of:
   receiving a request for information from a remotely located information requestor, the request associated with information controlled by an information controller and specifying a designated purpose thereby providing the requested information, the designated time for providing the requested information, and a request life span for the providing access to the requested information;
   initiating a transaction to handle the request in accordance with the designated purpose, the designated time, and the request life span, wherein the transaction identifies at least one remotely located information recipient to receive a request result, wherein the transaction actuates a plurality of tasks to be performed by a plurality of distinct information providers, each task being performed by a corresponding information provider different from the information requestor and information controller, and wherein the transaction determines for each task a start time when the task is to be commenced and a delivery time that determines when a task result that is tailored for information privileges granted to the information recipient by the information controller in accordance with the designated purpose is to be conveyed from the corresponding information provider to the information recipient such that the information service sends the plurality of tasks to the plurality of distinct information providers which process the tasks and subsequently respond to the information service with a plurality of task results that are then conveyed to the information recipient within the start time and an end time corresponding to the request life span;
   generating a plurality of transaction identifiers, each transaction identifier specifying (a) a transaction type, (b) at least one of the plurality of information providers, (c) a particular task to be performed by a particular information provider, (d) a time when the particular task is to be performed, (e) a location at which a result of the particular task performed is to be conveyed, (f) a time at which a particular task result is to be returned to the information service within the request life span, and (g) a task life span during which the particular task result is valid, the particular task result being disposed of at an end of the task life span;
   querying a record store for information associated with the information controller and associated with the designated purpose, wherein the information requestor and the information recipient are not authorized to directly access content of the record store;
   generating at least one request result based at least in part upon information returned from the querying step, each request result corresponding to an information recipient and tailored for information privileges of the information recipient, wherein the information privileges are established by the information controller; and
   conveying the at least one request result to the information recipient proximate to the designated time for providing the requested information, wherein the conveyed request result has an associated delete time at which time the request result is deleted from a data store accessible by the information recipient.

2. The method of claim 1, wherein the designated purpose is a business transaction between the information controller and the information recipient.

3. The method of claim 2, wherein the record store includes at least one of confidential and protected privacy information of the information controller.

4. The method of claim 2, wherein the information requestor is the information controller.

5. The method of claim 2, wherein the information requestor is the information recipient.

6. The method of claim 5, wherein at least one information recipient includes a different information recipient, wherein the different information recipient is the information controller.

7. The method of claim 1, further comprising the step of:
   the transaction conveying a task query to a remotely located information provider and responsively receiving a task response, wherein the generating step generates the at least one result based at least in part upon the task response, and wherein the information provider is an entity other than the information requestor, the information controller, and the at least one information recipient.

8. The method of claim 7, wherein the information provider is not authorized to directly access content of the record store, and wherein the information provider is selected from the group consisting of an information service, an Internet resource, and a private network.

9. The method of claim 1, further comprising the step of:
   said transaction actuating a plurality of tasks, each task generating a task response, wherein the generating step generates the at least one result based at least in part upon the task responses.

10. A method for an information service to provide information at a later designated time comprising the steps of:
    receiving a request for information from a remotely located information requestor, the request associated with information controlled by an information controller and specifying a designated purpose thereby providing the requested information, the designated time for providing the requested information, and a request life span for the providing access to the requested information;
    initiating a transaction to handle the request in accordance with the designated purpose, the designated time, and the request life span, wherein the transaction identifies at least one remotely located information recipient to receive a request result, wherein the transaction actuates a plurality of tasks to be performed by a plurality of distinct information providers, each task being performed by a corresponding information provider different from the information requestor and information controller, and wherein the transaction determines for each task a start time when the task is to be commenced and a delivery time that determines when a task result that is tailored for information privileges granted to the information recipient by the information controller in accordance with the designated purpose is to be conveyed from the corresponding information provider to the information recipient such that the information service sends the plurality of tasks to the plurality of distinct information providers which process the tasks and subsequently respond to the information service with a plurality of task results that are then conveyed to the information recipient within the start time and an end time corresponding to the request life span;

the transaction generating a plurality of transaction identifiers, each transaction identifier specifying (a) a transaction type, (b) at least one of the plurality of information providers, (c) a particular task to be performed by a particular information provider, (d) a time when the particular task is to be performed, (e) a location at which a result of the particular task performed is to be conveyed, (f) a time at which a particular task result is to be returned to the information service within the request life span, and (g) a task life span during which the particular task result is valid, the particular task result being disposed of at an end of the task life span;

querying a record store for information associated with the information controller and associated with the designated purpose, wherein the information requestor and the information recipient are not authorized to directly access content of the record store;

generating at least one request result based at least in part upon information returned from the querying step, each request result corresponding to an information recipient and tailored for information privileges of the information recipient, wherein the information privileges are established by the information controller; and conveying the at least one request result to the information recipient proximate to the designated time for providing the requested information, wherein the information recipient and the information requestor comprise different entities, and wherein the conveyed request result has an associated delete time at which time the request result is deleted from a data store accessible by the information recipient.

11. A method for an information service to provide information at a later designated time to requestors comprising the steps of:

receiving a request for information from a remotely located information requestor, the request associated with information controlled by an information controller and specifying a designated purpose thereby providing the requested information, the designated time for providing the requested information, and a request life span for the providing access to the requested information;

initiating a transaction to handle the request in accordance with the designated purpose, the designated time, and the request life span, wherein the transaction identifies at least one remotely located information recipient to receive a request result, wherein the transaction actuates a plurality of tasks to be performed by a plurality of distinct information providers, each task being performed by a corresponding information provider different from the information requestor and information controller, and wherein the transaction determines for each task a start time when the task is to be commenced and a delivery time that determines when a task result that is tailored for information privileges granted to the information recipient by the information controller in accordance with the designated purpose is to be conveyed from the corresponding information provider to the information recipient such that the information service sends the plurality of tasks to the plurality of distinct information providers which process the tasks and subsequently respond to the information service with a plurality of task results that are then conveyed to the information recipient within the start time and an end time corresponding to the request life span;

the transaction generating a plurality of transaction identifiers, each transaction identifier specifying (a) a transaction type, (b) at least one of the plurality of information providers, (c) a particular task to be performed by a particular information provider, (d) a time when the particular task is to be performed, (e) a location at which a result of the particular task performed is to be conveyed, (f) a time at which a particular task result is to be returned to the information service within the request life span, and (g) a task life span during which the particular task result is valid, the particular task result being disposed of at an end of the task life span;

querying a record store for information associated with the information controller and associated with the designated purpose, wherein the information requestor and the information recipient are not authorized to directly access content of the record store;

generating at least one request result based at least in part upon information returned from the querying step, each request result corresponding to an information recipient and tailored for information privileges of the information recipient, wherein the information privileges are established by the information controller; and conveying the at least one request result to the information recipient proximate to the future time for providing the requested information, wherein the conveyed request result has an associated delete time at which time the request result is deleted from a data store accessible by the information recipient.

12. The method of claim 1, further comprising the steps of:

determining that the designated purpose has been satisfied; and responsive to the determining step, automatically deleting the request result from a data store accessible by the information recipient.

13. The method of claim 12, wherein the designated purpose comprises an appointment between the information recipient and the information controller.

14. A system for providing information at a later designated time comprising:

an information service system to provide results in response to submitted requests, each request associated with an information controller and specifying a designated purpose thereby providing the requested information, the designated time for providing the requested information, and a request life span for the providing access to the requested information, wherein each result is associated with a recipient and tailored to authorization privileges granted by the information controller to the recipient, wherein the information service system comprises a central repository including information not directly accessible by a remote system to which each result it conveyed, wherein each of the provided result for requests has an associated delete time at which time the provided results are deleted from a data store accessible by an information recipient that received the provided results;

the system initiating a transaction to handle each request in accordance with the designated purpose, the designated time, and the request life span, wherein the transaction identifies at least one remotely located information recipient to receive a request result, wherein the transaction actuates a plurality of tasks to be performed by a plurality of distinct information providers, each task being performed by a corresponding information provider different from the information requestor and information controller, and wherein the transaction determines for each task a start time when the task is to be commenced and a delivery time that determines when a task result that is tailored for information privileges granted to the information recipient by the information controller in accordance with the designated purpose is to be conveyed from the corresponding information provider to the information recipient such that the information service sends the plurality of tasks to the plurality of distinct information providers which process the tasks and subsequently respond to the information service with a plurality of task results that are then conveyed to the information recipient within the start time and an end time corresponding to the request life span;

the system further generating a plurality of transaction identifiers, each transaction identifier specifying (a) a transaction type, (b) at least one of the plurality of information providers, (c) a particular task to be performed by a particular information provider, (d) a time when the particular task is to be performed, (e) a location at which a result of the particular task performed is to be conveyed, (f) a time at which a particular task result is to be returned to the information service within the request life span, and (g) a task life span during which the particular task result is valid, the particular task result being disposed of at an end of the task life span.

15. The system of claim 14, wherein the information service system determines when the designated purpose has been completed, wherein results associated with the designated purpose are removed from the remote system to which each result is conveyed upon the determination that the designated purpose has been completed.

16. The system of claim 14, wherein the central repository comprises:
a record store including information controlled by a plurality of information controllers and used by the information service system to provide results for requests, wherein information recipients are not granted direct access to content of the record store.

17. The system of claim 14, wherein the central repository comprises:
at least one intelligent agent that is a software agent to manage a transaction, wherein a transaction is initiated by the request and responsively generates at least one of said results.

18. An information client for presenting information at a later designated time comprising:
an information presentation application for presenting results supplied by a remotely located information service system at the designated time, wherein the results are generated by the information service system responsive to information requests from a source other than the information client, wherein said results are specifically tailored to privileges an information controller granted to an information recipient corresponding to the information presentation application, wherein said results are automatically deleted upon the occurrence of an event, wherein the information presentation application is configured so as to be unable to retain a local copy of the results after the occurrence, wherein each result generated by the information service system has an associated delete time at which time the result is deleted from a data store accessible by the information presentation application;

wherein the information service system generates the results by initiating a transaction to handle each request in accordance with a designated purpose thereby providing information, the designated time for providing the information, and a life span for providing access to the information specified in each request, wherein the transaction identifies at least one remotely located information recipient to receive a request result, wherein the transaction actuates a plurality of tasks to be performed by a plurality of distinct information providers, each task being performed by a corresponding information provider different from the information requestor and information controller, and wherein the transaction determines for each task a start time when the task is to be commenced and a delivery time that determines when a task result is to be conveyed from the corresponding entity to at least one other entity such that the corresponding entity sends the plurality of tasks to the plurality of distinct entities which process the tasks and subsequently respond to the information service with a plurality of task results that are then conveyed to the information recipient within the start time and an end time corresponding to the request life span; and wherein the information service system is further configured to generate a plurality of transaction identifiers, each transaction identifier specifying (a) a transaction type, (b) at least one of the plurality of information providers, (c) a particular task to be performed by a particular information provider, (d) a time when the particular task is to be performed, (e) a location at which a result of the particular task performed is to be conveyed, (f) a time at which a particular task result is to be returned to the information service within the limited time, and (g) a task life span during which the particular task result is valid, the particular task result being delivered proximate to the designated time for providing the requested information and being disposed of at an end of the task life span.

19. The information client of claim 18, further comprising:
a presentation engine for presenting the results;
a receiving engine for receiving the results from the information service system; and
a disposal engine for automatically deleting results from the information client upon the occurrence of the event, the occurrence established by the information service system.

* * * * *